(12) United States Patent
Hadden, Jr.

(10) Patent No.: US 12,263,093 B2
(45) Date of Patent: *Apr. 1, 2025

(54) DYNAMIC SPINAL SEGMENT REPLACEMENT

(71) Applicant: MEDSMART INNOVATION, INC., Houston, TX (US)

(72) Inventor: Anthony Hadden, Jr., Bend, OR (US)

(73) Assignee: MEDSMART INNOVATION, INC., Houston, TX (US)

( * ) Notice: Subject to any disclaimer, the term of this patent is extended or adjusted under 35 U.S.C. 154(b) by 206 days.

This patent is subject to a terminal disclaimer.

(21) Appl. No.: 18/075,187

(22) Filed: Dec. 5, 2022

(65) Prior Publication Data

US 2023/0099613 A1    Mar. 30, 2023

Related U.S. Application Data

(63) Continuation of application No. 16/681,542, filed on Nov. 12, 2019, now Pat. No. 11,517,442, which is a continuation of application No. 15/975,622, filed on May 9, 2018, now Pat. No. 10,507,115, which is a
(Continued)

(51) Int. Cl.
*A61F 2/44* (2006.01)
*A61F 2/30* (2006.01)

(52) U.S. Cl.
CPC .............. *A61F 2/4425* (2013.01); *A61F 2/44* (2013.01); *A61F 2/442* (2013.01); *A61F 2/4455* (2013.01); *A61F 2/446* (2013.01); *A61F 2002/30062* (2013.01); *A61F 2002/30187* (2013.01); *A61F 2002/30228* (2013.01); *A61F 2002/30232* (2013.01); *A61F 2002/30235* (2013.01); *A61F 2002/30405* (2013.01); *A61F 2002/3052* (2013.01); *A61F 2002/30525* (2013.01); *A61F 2002/3055* (2013.01); *A61F 2002/30556* (2013.01); *A61F 2002/30563* (2013.01); *A61F 2002/30565* (2013.01); *A61F 2002/30579* (2013.01); *A61F 2002/30601* (2013.01); *A61F 2002/30649* (2013.01); *A61F 2002/30677* (2013.01); *A61F 2002/30797* (2013.01); *A61F 2002/30807* (2013.01); *A61F 2002/30884* (2013.01); *A61F 2002/3093* (2013.01); *A61F 2002/443* (2013.01); *A61F 2310/00017* (2013.01); *A61F 2310/00023* (2013.01); *A61F 2310/00029* (2013.01); *A61F 2310/00179* (2013.01); *A61F 2310/00293* (2013.01);
(Continued)

(58) Field of Classification Search
CPC .. A61F 2/44; A61F 2/442; A61F 2/447; A61F 2/4425; A61F 2/446; A61F 2/4455; A61F 2/30
See application file for complete search history.

(56) References Cited

U.S. PATENT DOCUMENTS 7,819,922 B2 * 10/2010 Sweeney ............... A61F 2/44
                                                  623/17.15
10,507,115 B2 * 12/2019 Hadden, Jr. ........... A61F 2/4455
(Continued)

*Primary Examiner* — Christopher J Beccia
(74) *Attorney, Agent, or Firm* — Polsinelli PC

(57) ABSTRACT

A vertebral body system and method having a polyaxial fastener receiving member, adjustable width plates and a pedicle screw having a pedicle threaded portion and a threaded portion for fastening to the vertebral body.

17 Claims, 6 Drawing Sheets

Related U.S. Application Data continuation of application No. 14/213,856, filed on Mar. 14, 2014, now Pat. No. 9,968,460.

(60) Provisional application No. 61/799,672, filed on Mar. 15, 2013.

(52) U.S. Cl.
CPC ............ *A61F 2310/00329* (2013.01); *A61F 2310/00359* (2013.01)

(56) References Cited

U.S. PATENT DOCUMENTS

| | | | | |
|---|---|---|---|---|
| 2005/0245933 A1* | 11/2005 | Sevrain | ............. | A61B 17/7059 606/328 |
| 2009/0112269 A1* | 4/2009 | Lieberman | ......... | A61B 17/8625 606/301 |

* cited by examiner

DYNAMIC SPINAL SEGMENT REPLACEMENT

CROSS REFERENCE TO RELATED APPLICATIONS

This application is a continuation of U.S. patent application Ser. No. 16/681,542, filed Nov. 12, 2019, which is a continuation of U.S. patent application Ser. No. 15/975,622, filed May 9, 2018, now U.S. Pat. No. 10,507,115, which is a continuation of U.S. patent application Ser. No. 14/213,856, filed on Mar. 14, 2014, now U.S. Pat. No. 9,968,460, which claims the benefit of U.S. Provisional Application No. 61/799,672 filed Mar. 15, 2013, the contents of each of the aforementioned applications are hereby incorporated by reference in their entirety.

FIELD OF THE INVENTION

The present disclosure relates generally to the field of orthopedic medical implants, and more particularly relates to an expandable implant and method for replacing structures such as vertebral bodies and intervertebral discs.

BACKGROUND OF THE INVENTION

The human spine serves as the main structural weight bearing support of the human skeleton. The spinal column comprises a plurality of vertebrae separated by intervertebral discs. Moving down the spinal column, five distinct regions exist as follows: cervical, thoracic, lumbar, sacral, and coccygeal. The cervical region comprises seven vertebra; the thoracic region, twelve; the lumbar region, five; the sacral, five; and the coccygeal, four. The cervical, thoracic, and lumbar vertebrae generally remain separate throughout an individual's lifetime whereas the sacral and coccygeal vertebrae fuse to form the sacrum and coccyx, respectively. In general, each vertebra consists of an anterior, cancellous, portion and a posterior arch, comprising two pedicles and two laminae, which support seven processes (four articular, two transverse, and one spinous). The spinal cord runs through a passageway between the anterior and posterior portions of the vertebrae.

When vertebrae and/or intervertebral discs become compromised by trauma, disease, or degeneration, the ability for the spinal column to effectively serve it weight bearing support function is diminished. Furthermore, the spinal cord or nerve roots may subsequently become impinged. As a result, an individual may experience debilitating pain, loss of spinal column stability, and/or reduced range of motion (i.e. flexion, rotation, and extension) of the spinal column. To alleviate these issues, removal and replacement of the compromised vertebrae and intervertebral discs is often required if other non-invasive methods (i.e. drug treatment or physical therapy) prove unavailing.

One common type of vertebral injury is a burst fracture of the thoracic or lumbar portion of the spine, mainly involving the anterior and middle columns, and often occurring in instances of trauma or pathologically from primary or secondary neoplasms. With significant degeneration, spinal surgery becomes necessary for treating the patient. In the past, surgical goals involved spinal stabilization and/or correction of coronal sagittal balance. Accordingly, involved techniques were directed to stabilization of the abnormality and "fusion" techniques. These techniques involve fusing or "freezing" the segment in its position, despite being an abnormal position, in order to prevent progressively worse conditions and to assist in pain relief. This, however, leads to chronic pain as well as progression of abnormal spinal wear and tear, resulting in degeneration of adjacent levels of fused segments. This results in the return of the patient to potentially multiple surgeries finally resulting in Failed Back Surgery Syndrome.

Recent techniques to some degree have taken into consideration the natural balancing of the body. In these, spinal deformity correction surgery is aimed at reestablishing normal physiological coronal and sagittal balance and preserving natural motion of the body. However, even these more recent procedures still fail to take in account many aspects for providing optimal techniques consistent with the body's natural balance and anatomy.

SUMMARY OF THE INVENTION

In one example, disclosed herein is a vertebral implant assembly including:
a prosthetic vertebral body for insertion into a spinal column, the prosthetic vertebral body having a fastener receiving member;
a pedicle fastener having at least two distinct fastening portions, the distinct fastening portions comprising a first fastening portion receivable by the fastener receiving portion of the prosthetic vertebral body, and a second fastening portion configured to fasten to cancellous bone.

In one example, disclosed herein is a vertebral implant apparatus including:
a prosthetic vertebral body for insertion into a spinal column, the vertebral body having a vertical axis aligned in the general longitudinal direction of the spinal column when inserted therein;
a polyaxial receiver attached to said prosthetic vertebral body, and shaped for receiving a pedicle fastener.

In one example, disclosed herein is a vertebral implant apparatus including:
a prosthetic vertebral body for insertion into a spinal column, the vertebral body having a vertical axis aligned in the general longitudinal direction of the spinal column when inserted therein;
a receiver shaped for receiving a pedicle fastener, wherein the receiver is movably adjustable in a horizontal axis perpendicular to the vertical axis of the prosthetic vertebral body to facilitate alignment with pedicles upon insertion into the spinal column.

In another exemplary aspect, processes for implanting a prosthetic vertebral body are also provided. In general, the prosthetic vertebral body may be inserted into a vertebral cavity corresponding to the removed compromised vertebra and adjacent intervertebral discs. The prosthetic vertebral body may then be connected to pedicles by multi-threaded pedicle screws which are cooperatively engaged with the fastener receiving members of the prosthetic vertebral body.

Other additional devices, apparatus, structures, and processes are described by reference to the drawings and detailed descriptions herein.

BRIEF DESCRIPTION OF THE DRAWINGS

Various embodiments in accordance with the present disclosure will be described with reference to the drawings, in which.

DETAILED DESCRIPTION

A detailed description of embodiments of the present process is disclosed herein. However, it is to be understood that the disclosed embodiments are merely exemplary of the process and that the process may be embodied in various and alternative forms of the disclosed embodiments. Therefore, specific procedural, structural and functional details which are addressed in the embodiments disclosed herein are not to be interpreted as limiting, but merely as a basis for the claims and as a representative basis for teaching one skilled in the art to variously employ the present disclosure.

In one or more exemplary embodiments there is disclosed herein a system and method for implantation of prosthetic vertebral bodies and optionally intervertebral discs ("hereinafter discs"). Disclosed herein also are multiple exemplary embodiments involving replacement of vertebral bodies employing minimally invasive techniques. As described herein, the prosthetic vertebral bodies and discs are preferably dynamically integrated to provide for the maintenance of natural anatomy and balance of forces in the vertebral column.

Figure 1:
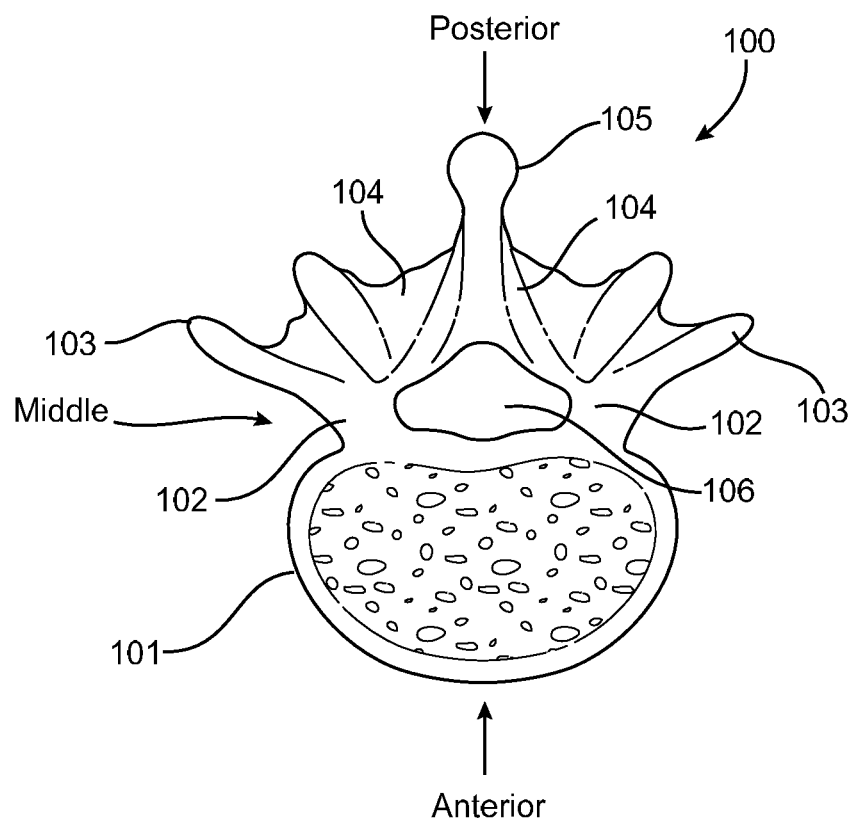
FIG. 1 is an overhead view of a human vertebra.

Shown in FIG. 1 is an exemplary generally healthy vertebra 100 as typically found in the human body. The vertebra 100 includes the vertebral body 101 set in the anterior portion of the vertebra, with the anterior being directed toward the lower portion of FIG. 1 and the posterior being directed toward the upper portion of FIG. 1. The vertebral body 101 is generally cylindrical, containing a hard bony outer cortical rim and less dense cancellous bone within. Two pedicles 102 extend from the vertebral body 101 toward the posterior portion to the transverse process 103. A pair of lamina 104 extends from the transverse process 103 to the spinous process 105 at the posterior of the vertebra. The vertebral foramen 106 is formed between the pedicles 102 and lamina 104 wherein the spinal cord and meninges are housed.

Figure 2:
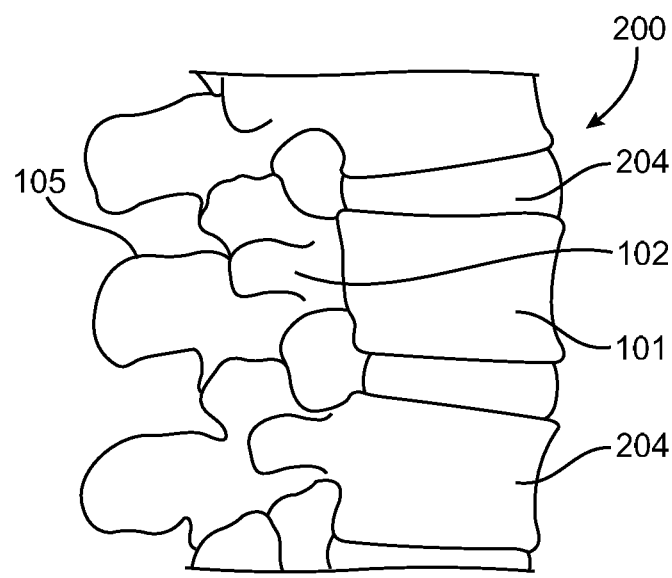
FIG. 2 is a side view of a portion of a spinal column containing a compromised vertebra.

Shown in FIG. 2 is a lateral side view of several adjacent vertebral segments forming a vertebral column 200 in the thoracic region as typically found in the human body. The vertebral column comprises a vertebral body 101 in the anterior portion of the vertebra. Pedicles 102 are illustrated extending dorsally from the vertebral body 101, and shown in the posterior portion of the vertebral column are spinous process 105. Adjacent intervertebral discs 204 are also represented immediately above and below the vertebral body 101.

Figure 3:
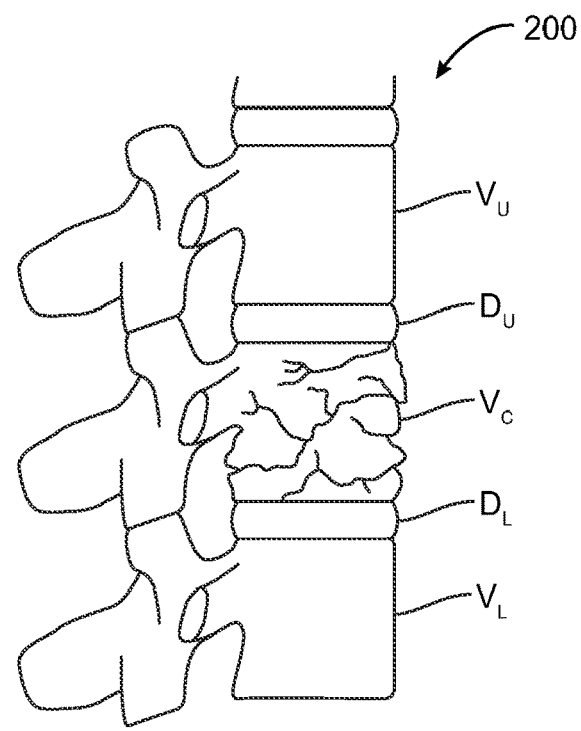
FIG. 3 is a lateral side view of a portion of a spinal column containing a compromised vertebra.

Referring to FIG. 3, shown therein is a lateral side view of a portion of vertebral column 200, illustrating a vertebral body segment with a burst fracture. Burst fractures are particularly severe because the fracture extends in all directions of the body. The vertebral body with the burst fracture can be referred to as a compromised vertebral body, $V_C$, and is located adjacent to upper and lower intervertebral discs $D_U$ and $D_L$, and between adjacent upper and lower vertebra $V_U$ and $V_L$. Although a burst fracture is shown in FIG. 1, the particular reason for removal of the compromised vertebral body is not limited herein, and can include any type of fracture, degeneration, deformity, pathology, or various other bases which may lead to instability or defectiveness and the eventual medical decision for surgical removal.

Figure 4:
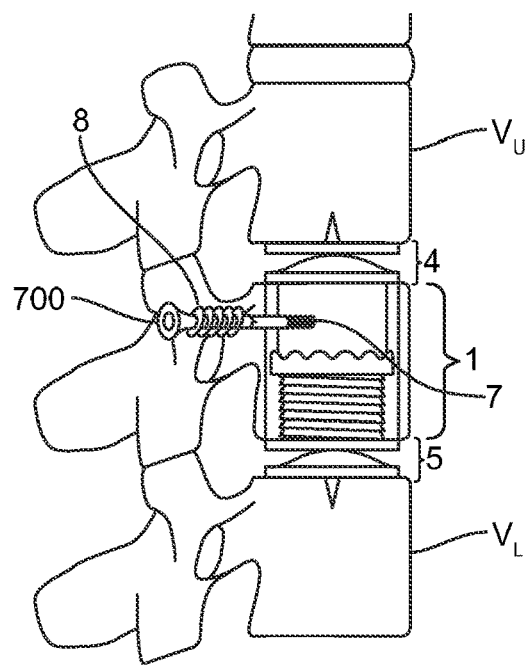
FIG. 4 is a lateral side view of one exemplary embodiment of a prosthetic vertebral body.

As disclosed herein, the compromised vertebral body and any adjacent discs can be surgically replaced with a prosthetic vertebral body and optionally synthetic discs. Illustrated in FIG. 4 is a lateral side view of the portion of the vertebral column of FIG. 3 with the exception, however, that the compromised vertebral body $V_C$ of FIG. 3 has been removed along with adjacent discs $D_U$ and $D_L$ and replaced with one exemplary embodiment of a prosthetic vertebral body 1 along with adjacent artificial disc assemblies 4 and 5.

Figure 5:
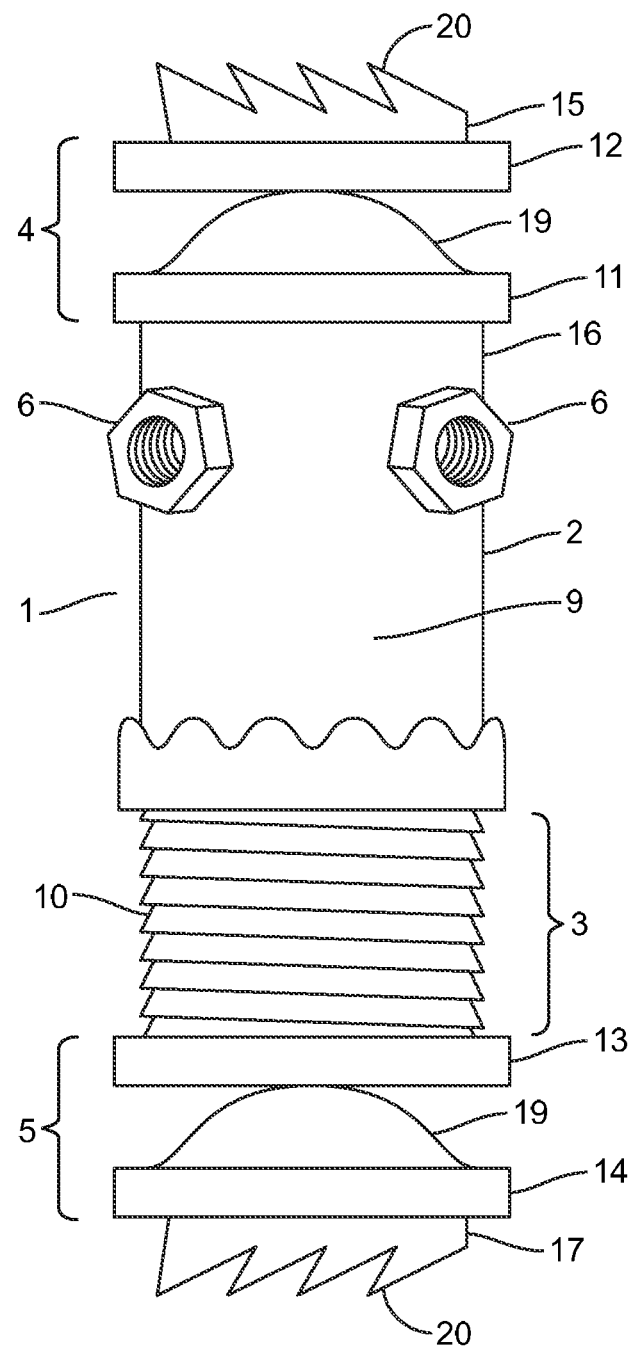
FIG. 5 is a posterior view of one exemplary embodiment of a prosthetic vertebral body.

FIG. 5 is a posterior view illustrating one exemplary embodiment of a prosthetic vertebral body 1 for replacing structures such as vertebrae and intervertebral discs. The vertebral body can also be referred to as a "cage" or a "spacer." The cage can be a single integrated unit or can be an assembly of two or more parts. The cage can be made up of a hard biocompatible material which can withstand the stresses normally associated with the vertebral column. Accordingly, the material can include metal, alloys or plastic, including titanium alloys, or plastics such as polyether ether ketone (PEEK).

The cage can also be an expandable vertebral body, thus allowing adjustment to various heights to suit the patient's proportions. Exemplary expandable cages are known in the art and include for example those described in U.S. Pat. Nos. 8,241,294, 8,197,546, and 7,691,147. With respect to expandability of the cage, similar mechanisms can be applied herein or modified for dynamic replacement as described herein.

As shown in the illustrated embodiment of FIG. 5, the prosthetic vertebral body 1 is generally cylindrical and includes a sleeve member 2 and an inner base member 3. The inner base member has a threaded surface 10 to allow advancement into the sleeve member 2. The sleeve member 2 has a threaded central aperture (not shown) on its internal surface to allow the sleeve member 2 and the inner base member 3 to operatively engage each other. Accordingly, the longitudinal dimension of the prosthetic vertebral body 1 may be altered by varying the degree to which the inner base member 3 is enveloped within the threaded central aperture (not shown) of the outer cage 2.

In other embodiments, the outer threaded surface 10 can instead be a series of ratchet notches which face the inner wall of the sleeve member 2 when inserted therein. In such case, the inner surface of the sleeve member 2 has projections to engage the notches, and thus mate with the notches of the outer surface of the inner base member 3. This allows for adjustment, and a blocking member (not shown) can be engaged with the ratchet notches to lock the sleeve member 2 and inner base member 3 in place. Such locking members are described for example in U.S. Pat. No. 8,241,294.

Although the outer surface 9 of the sleeve member 2 is cylindrical or tubular in shape, in alternative embodiments the sleeve member 2 can take the form of rectangle, square, ellipse, diamond, oval, D-shape, or any shape desired to conform and substantially match the bone structure of the compromised vertebra being replaced. The outer surface 9 can be roughened or corrugated, or can have a plurality of recesses or apertures running therethrough.

Shown in the exemplary embodiment of FIG. 5 are two polyaxial fastener receiving members 6 which are pivotally attached and protrude radially outward from the outer cage outer surface 9 for operatively receiving a fastening member. Polyaxial refers to the ability of the receiving members 6 to swivel, pivot or move in multiple axes, including vertical and horizontal, or in any direction, including a 360 degree swivel rotation, pivot or movement relative the vertebral body. The entire fastener receiving member 6 can be pivotal, or a portion, or a head portion thereon. This provides the doctors dynamic implantation, as the different proportions of the human body can be accommodated during surgery.

In the exemplary embodiment shown in FIG. 5, the replacement of the vertebral body can further comprise replacement of the adjacent discs. Accordingly, replacement further comprises insertion of an upper (superior) artificial disc assembly 4 connected to the top portion of the outer cage 2 and a lower (inferior) artificial disc assembly 5 connected to the bottom portion of the inner member 3. The disc assemblies 4 and 5 can be permanently attached to, or integrated with, the upper (superior) and lower (inferior) portions of the vertebral body 1, or can be removable, or separately placed without attachment above or below the vertebral body 1 when implanting the device. For example, the disc assemblies 4 and 5 can be removably joined with the use of mating surfaces with one or more corresponding projections and/or one or more corresponding recesses on the surface of the prosthetic vertebral body 1 and disc assemblies 4 and 5. Thus, the manner in which the disc assembles 4 and 5 are joined with the prosthetic vertebral body 1 are not particularly limited.

In the exemplary embodiments, the upper artificial disc assembly 4 comprises a first upper endplate 11, a second upper endplate 12, and a ball and socket joint 19 between the endplates 11 and 12. The ball and socket joint 19 provides mobility between vertebral bodies which are otherwise absent in fused procedures. Such invertebral discs are known and commercially available in the art, such as for example ProDisc-L by Synthes®. Alternatively, the portion between the endplates 11 and 12 can comprise a compressible portion therebetween, preferably made of a biocompatible elastomeric material. Alternatively, the intervertebral discs can be constructed of, or contain, a polymeric material, a spring mechanism, or any other comparable compressible means known or used by one of skill in the art to promote mobility of the spine.

The lower artificial disc assembly 5 comprises a first lower endplate 13, a second lower endplate 14, and a ball and socket joint 19 therebetween. One or more protruding members 20 are permanently affixed on the bone side each of endplate surfaces 15 and 17 respectively. The protruding members 20 fit against the healthy vertebrae, $V_U$ and $V_L$, adjacent to the removed compromised vertebrae, $V_C$, and the removed intervertebral discs, $D_U$ and $D_L$, and anchor the prosthetic vertebral body 1 in the correct vertical orientation.

In an alternative embodiment the first upper endplate 11 and the first lower endplate 13 are affixed to vertebral body 1 respectively by one or more rotating members. The rotating members will allow for horizontal rotation of the artificial disc assemblies 4 and 5 to ensure proper orientation with the adjacent vertebrae $V_U$ and $V_L$ respectively.

In the exemplary embodiment shown in FIG. 5, the protruding members 20 are in the form of a keel. The cross-sectional profile of the keel can have different shapes. For instance, the cross-sectional profile of the keel can have the shape of a wedge, a truncated wedge, a triangle, a truncated triangle, a rectangle, or a square. In alternative embodiments of the present disclosure, the protruding members 20 can be a rough surface, and/or a surface comprising ridges, spikes, raked or straight teeth, protrusions or any combination thereof.

In alternative embodiments, the second upper endplate 12 and the second lower endplate 14 are solid and smooth. In alternative embodiments of the present disclosure, the second upper endplate 12 and the second lower endplate 14 can be roughened or corrugated, or have a plurality of recesses or apertures running therethrough.

Figure 6:
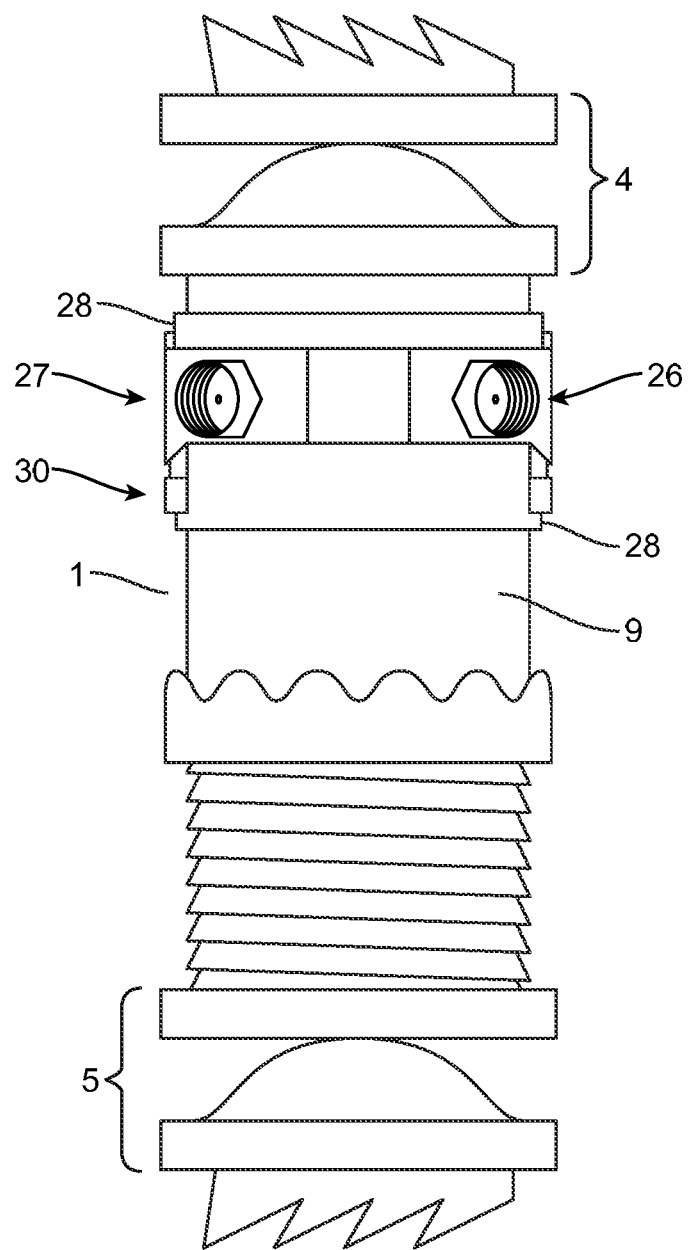
FIG. 6 is a posterior view of a prosthetic vertebral body of FIGS. 2 and 3 according to another embodiment.
Figure 7:
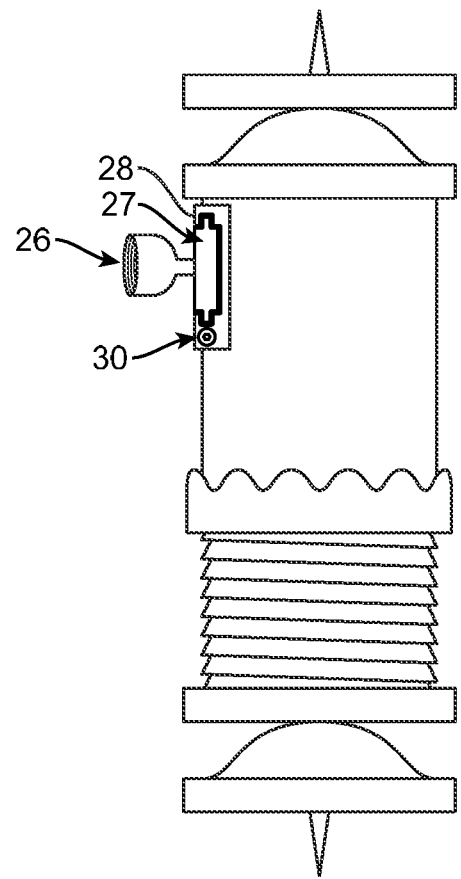
FIG. 7 is a lateral side view of one exemplary embodiment of a prosthetic vertebral body 6.
Figure 8:
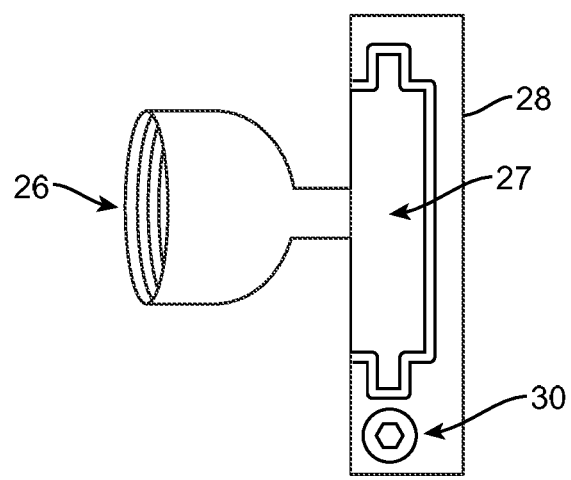
FIG. 8 is a lateral side view of one exemplary embodiment of a receiver shaped for receiving a pedicle fastener according to the prosthetic vertebral body of FIG. 6.
Figure 9:
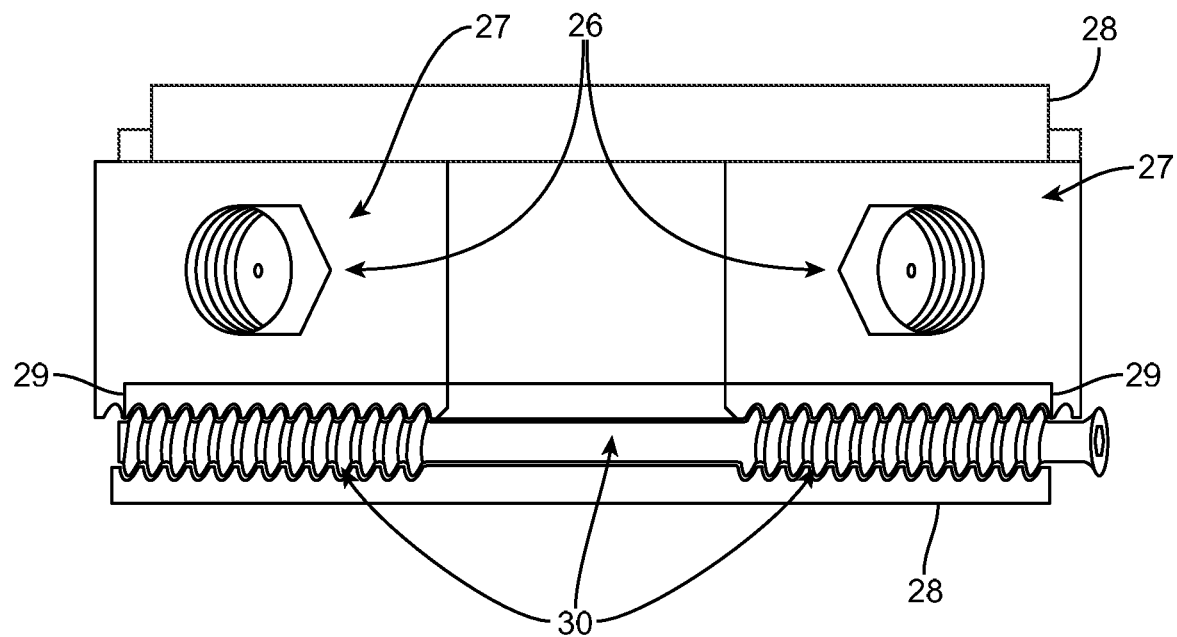
FIG. 9 is a posterior view of one exemplary embodiment of a receiver shaped for receiving a pedicle fastener according to the prosthetic vertebral body of FIG. 6.

FIG. 6 is a posterior view illustrating an exemplary embodiment of a prosthetic vertebral body 1 and intervertebral disc assemblies 4 and 5 for replacing structures such as vertebra and intervertebral discs. FIG. 7 displays a lateral view of embodiments of the prosthetic vertebral body 1 as shown in FIG. 6. FIGS. 8 and 9 display lateral and posterior views of the receiver shaped for receiving a pedicle fastener according to the prosthetic vertebral body 1 of FIG. 6 respectively. The polyaxial fastener receiving members 26 allow for variable angles of entry for the multithreaded screw shown in FIG. 10. Each polyaxial fastener receiving members 26 cooperatively connected to a first and second adjustable width plate 27. Each of the two adjustable width plates 27 are secured by a plate track 28 which is permanently affixed onto the outer cage outer surface 9. The adjustable width plates have serrated bottom portions 29 (shown in FIG. 9) which cooperatively interact with an adjustable width screw 30 contained within by the plate track 28. The adjustable width screw 30 has threads which are reversed for each plate such that the distance between the two adjustable width plates 27 can be altered by rotating the adjustable width screw 30 clockwise or counterclockwise along the length of the adjustable width screw 30.

Figure 10:
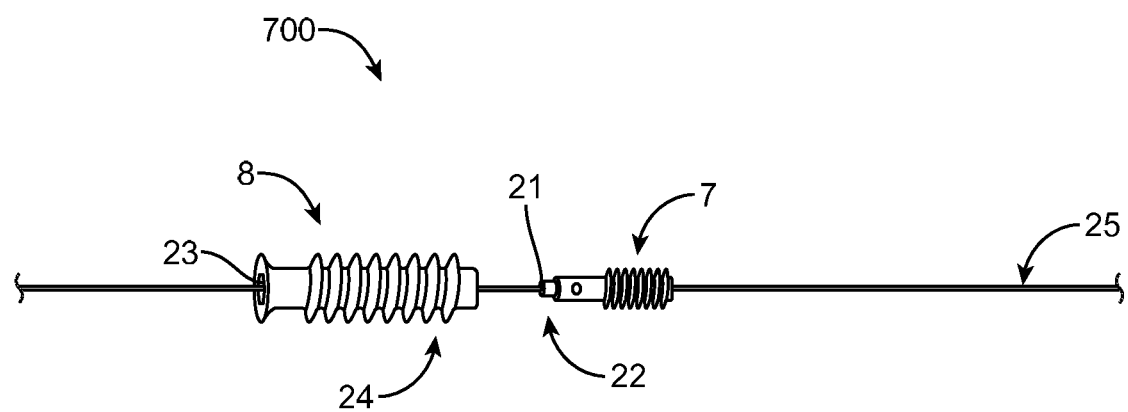
FIG. 10 is one exemplary embodiment of an unassembled pedicle screw disclosed herein.

FIG. 10 is an unassembled multi-threaded cannulated screw comprising the first vertebral body fastener 7 (also referred to as "VB fastener") and the second cancellous fastener 8 (also referred to as "cancellous fastener"). The VB fastener 7 further comprises a central aperture 21 running therethrough and a polygonal head 22. The VB fastener 7 is threaded to operatively interact with a fastener receiving member, such as polyaxial fastener receiving member 6 or 26 as shown in FIGS. 5 and 6 respectively. The VB fastener 7 can be threaded to interact with the polyaxial fastener receiving member which can be counterthreaded.

The cancellous fastener 8 comprises a central aperture 23 running therethrough and a locking means 24. The cancellous fastener 8 is threaded to operatively interact with a pedicle of the spinal column corresponding to the $V_c$, and in particular the cancellous bone within the pedicle.

The polygonal head 22 and the locking means 24 are fabricated to cooperatively engage each other to from a multi-threaded pedicle screw (hereinafter "the pedicle screw"—shown as 700 in FIG. 4). A guide wire 25 can be threaded through central apertures 21 and 23. The first fastening portion 7 is threaded to cooperatively engage the fastener receiving members 6 or 26 and is adapted for metal or plastic contact. The second fastening portion 8 is preferably cancellous threaded. The cancellous threaded portion may be in a form resembling any one of a cannulated screw, a pedicle screw, or a lag screw.

Conventional pedicle screws are not developed for attaching bone directly to hardware (i.e. prosthetic vertebral body). Accordingly, the joined pedicle screw described herein provides a first threaded portion for interaction with the metal or hard plastic of the receiving member on the prosthetic vertebral body and a second threaded portion for interaction with the cancellous bone (i.e. cancellous fastener) of the vertebra pedicle. The threaded portion for interaction with the prosthetic body is fine threaded, or machine threaded. Thus, this finer portion can have a greater number of threads, and smaller pitch (i.e. more threads per axial distance) relative the thread of the cancellous bone fastener. Additionally, such thread can have a smaller diameter relative the cancellous bone fastener. On the other hand, the cancellous bone is softer than the vertebral body or the metal/plastic receiving members and thus a machine-type thread may degenerate the cancellous bone over time. Accordingly, the portion of the screw to interact with the cancellous bone can have a thread typical for pedicle screws known in the art for fastening into cancellous bone. Accordingly, these will have a have a coarser thread, akin to a wood screw, and thus a larger pitch (i.e. fewer threads per axial distance) relative the VB fastener, or the portion of the screw interacting with the prosthetic vertebral body. Additionally, such thread can have a larger diameter relative the VB fastener.

Accordingly, the joined pedicle screw will have a finer thread toward its distal end for interaction with the vertebral body and a coarser end toward its proximal end for interaction with the cancellous bone in the pedicles. While in the illustrated embodiment, the VB fastener and cancellous fastener are two separate pieces, in alternative embodiments they can be one integral unit.

Embodiments of the prosthetic vertebral body 1, in whole or in part, can be constructed from any biocompatible material, including synthetic or natural autograft, allograft, or xenograft tissues, and can be resorbable or non-resorbable in nature. Tissue materials can include, for example, hard tissues, connective tissues, demineralized bone matrix, and combinations thereof. Resorbable materials such as, for example, polylactide, polyglycolide, polyorthoester, polyphosphazene, tyrosine-derived polycarbonate, bioactive glass, calcium phosphate, hydroxyapatite, and combinations thereof can be used. Non-resorbable materials such as, for example, non-reinforced polymers, carbon-reinforced polymer composites, PEEK and PEEK composites, titanium, titanium alloys, stainless steel, cobalt chrome allows, ceramics, and combinations thereof can be used.

For some embodiments of the prosthetic vertebral body 1 it may be advantageous, in some circumstances, to pack the outer cage outer surface 9 and areas between the second upper endplate 12 and the second lower endplate 14 and their adjacent vertebrae, $V_U$ and $V_L$, respectively, with a suitable osteogenic material and/or therapeutic composition. Suitable osteogenic materials can include, for example, autograft, allograft, xenograft, demineralized bone, synthetic and natural bonegraft substitutes, such as bioceramics, polymers and osteoinducive factors. These materials can be prepacked into, or onto, the prosthetic vertebral body 1 where surfaces are roughened or corrugated, or have a plurality of recesses or apertures running therethrough. A separate carrier such as, for example, collagen-based carriers, bioceramic materials, calcium phosphate, hydroxyapatite, or any combination thereof, can be used to hold the osteogenic materials in their desired location. The carriers can also be partially comprised of therapeutic or infection resistant agents. The carriers can also be partially comprised of an effective amount bone morphogenic protein, transforming growth factor β1, insulin-like growth factor 1, platelet-derived growth factor, fibroblast growth factor, LIM mineralization protein (LMP), and any combinations thereof.

In other embodiments however, no osteogenic material is employed as to avoid fusion of the adjacent vertebra and to maintain flexibility based on the prosthetic device disclosed herein.

An exemplary embodiment for the lateral implant of the prosthetic vertebral body 1 is disclosed herein involving a minimally invasive percutaneous method. A patient can be laid on his or her side and a corpectomy performed, wherein the compromised vertebral body $V_C$ and adjacent discs $D_U$ and $D_L$ are removed. The prosthetic vertebral body 1 is placed in a portion of a spinal column where a compromised vertebra, $V_C$, and its adjacent intervertebral discs, $D_U$ and $D_L$, were located before removal of said compromised vertebra and intervertebral discs.

A jamshidi needle can be employed to burrow through one or both remaining pedicles to the vertebral body 1. A guide wire 25 can then be attached or placed proximate to fastener receiving member 6 of the prosthetic vertebral body 1. The first vertebral body fastener 7, as it has a central aperture 21, can be placed over the guide wire and slid through the pedicle to the fastener polyaxial receiving member 26 of vertebral body 1. The first vertebral body fastener 7 can be fastened, screwed or attached to the polyaxial receiving member 26.

Next, the second cancellous fastener 8 can be screwed into the pedicle. As the second cancellous fastener 8 has wider threads than the first vertebral body fastener 7, and also being threaded for cancellous bone, it will affix within the pedicle as it is tightened. As second cancellous fastener 8 passes through the pedicle, its distal end closest to the vertebral body 1 will contact the first vertebral body fastener 7. Fasteners 7 and 8 can then attach to one another, either through entrance of the polygonal head of first vertebral body fastener 7 into a receiving portion in the second cancellous fastener 8. Alternatively, these can be fastened together by threading, or via reciprocal male female portions on either of the fasteners. The polygonal head can allow both the vertebral body fastener 7 and second cancellous fastener 8 to rotate together and be fixed within the pedicle and polyaxial receiving member respectively. Thereafter, the guide wire can be removed. This process is repeated, either sequentially or concurrently, to fasten the prosthetic vertebral body 1 to two pedicles.

Alternatively or additionally, when inserting the vertebral body 1, the adjustable width plates 27 can be moved closer or further apart by rotating the adjustable width screw 30 clockwise or counterclockwise to optimize the placement of the prosthetic vertebral body 1 in accordance with the patient's anatomical interpedicular width. Additionally, vertical adjustment can be made by inserting prosthetic invertebral discs, disclosed herein, of varying widths.

With respect to another embodiment of the present disclosure, after fastening the multi-threaded screws into their corresponding pedicles, the adjustable width plates 27 can be moved closer or further apart by rotating the adjustable width screw 30 clockwise or counterclockwise to optimize the placement of the prosthetic vertebral body 1 in accordance with the patient's anatomical interpedicular width.

After fastening the multi-threaded screw into the pedicles, if using the second and additionally optimizing the placement of the prosthetic vertebral body 1 in accordance with the patient's anatomical interpedicular width, the vertical height of the prosthetic vertebral body 1 can be expanded to fit the vertebral cavity once containing the compromised vertebra and adjacent intervertebral discs. During expansion of the prosthetic vertebral body 1, the artificial disc assemblies 4 and 5 can be acted upon to ensure proper orientation and attachment to adjacent upper and lower vertebrae, $V_U$ and $V_L$, respectively. Additionally, different artificial disc assemblies can be used to ensure proper orientation and attachment to adjacent upper and lower vertebrae as well as the proper orientation and attachment to the pedicles. Finally, if the incorporation of osteogenic materials and/or therapeutic compositions is advantageous they may be incorporated to the relevant components before, during, and/or after expansion of the prosthetic vertebral body 1.

As will be appreciated, numerous other various and combinations of the features discussed above can be employed without departing from the present disclosure. While embodiments of the present disclosure have been described in detail, the disclosure is considered to be illustrative and not restrictive in character. All changes and modification that come within the spirit of the disclosure are to be considered within the scope of the disclosure.

The invention claimed is:

1. A vertebral implant assembly comprising:
a prosthetic vertebral body for insertion into a spinal column, said prosthetic vertebral body having a fastener receiving member; and
a pedicle fastener having at least two distinct fastening portions, said distinct fastening portions comprising a first fastening portion receivable by the fastener receiving member of the prosthetic vertebral body, and a second fastening portion configured to fasten to cancellous bone,
wherein the first fastening portion is insertable to a threaded end of said second fastening portion.

2. The vertebral implant assembly of claim 1 wherein the diameter of threads on said second fastening portion is greater than the diameter of any part of the first portion.

3. The vertebral implant assembly of claim 1 wherein a threaded portion of the first fastening portion has a greater number of threads per axial distance than the second fastening portion.

4. The vertebral implant assembly of claim 1, wherein the second fastening portion is cancellous threaded and the thread on the first fastening portion is configured to fasten to a metal or plastic contact.

5. The vertebral implant assembly of claim 1, wherein the first fastening portion is attachable to the second fastening portion to form an integrated pedicle fastener.

6. The vertebral implant assembly of claim 1, wherein the first fastening portion is attachable to an end of said second fastening portion.

7. The vertebral implant assembly of claim 1, wherein the first fastening portion and second fastening portion form one integral unit.

8. The vertebral implant assembly of claim 1, wherein the first fastening portion and second fastening portion are distinct connectable units, which join to form the pedicle fastener.

9. The vertebral implant assembly of claim 1, wherein the fastener receiving member is threaded to receive the first fastening portion.

10. The vertebral implant assembly of claim 1, wherein a portion of the first fastening portion is insertable to an end of said second fastening portion.

11. The vertebral implant assembly of claim 1 further comprising a guide wire insertable through a central aperture.

12. The vertebral implant assembly of claim 1, said assembly further comprising an artificial disc configured to insert adjacent said prosthetic vertebral body in a spinal column.

13. The vertebral implant assembly of claim 12, wherein the artificial disc has pivoting or compressible portions to facilitate range of motion of a spinal column when the artificial disc is inserted in the spinal column.

14. The vertebral implant assembly of claim 12, wherein the artificial disc comprises a compressible elastomeric portion.

15. The vertebral implant assembly of claim 1, wherein the prosthetic vertebral body is expandable in vertical direction in the longitudinal direction of the spine when inserted therein.

16. A vertebral implant assembly comprising:
a prosthetic vertebral body for insertion into a spinal column, said prosthetic vertebral body having a fastener receiving portion; and
a pedicle fastener having at least two distinct fastening portions, said distinct fastening portions comprising a first fastening portion receivable by the fastener receiving portion of the prosthetic vertebral body, and a second fastening portion configured to fasten to cancellous bone,
wherein a non-cancellous bone end of the second fastening portion is configured to be attached to a non-prosthetic vertebral body end of the first receiving portion.

17. A vertebral implant assembly of claim 16, wherein the second fastening portion is cancellous threaded and the thread on the first fastening portion is configured to fasten to a metal or plastic contact.

* * * * *